US008622948B2

(12) United States Patent
Gedeon

(10) Patent No.: US 8,622,948 B2
(45) Date of Patent: Jan. 7, 2014

(54) ANATOMY SUPPORT DEVICE

(76) Inventor: Christina Gedeon, Manchester, MD (US)

( * ) Notice: Subject to any disclaimer, the term of this patent is extended or adjusted under 35 U.S.C. 154(b) by 31 days.

(21) Appl. No.: 13/423,750

(22) Filed: Mar. 19, 2012

(65) Prior Publication Data

US 2013/0245529 A1  Sep. 19, 2013

(51) Int. Cl.
*A61F 13/06* (2006.01)
(52) U.S. Cl.
USPC .................. 602/61; 602/67; 602/70
(58) Field of Classification Search
USPC ............. 602/68–71, 61; 128/96.1, 98.1, 99.1, 128/100.1, 101.1, 102.1
See application file for complete search history.

(56) References Cited

U.S. PATENT DOCUMENTS

| 265,672 | A | * | 10/1882 | Hart | 602/70 |
|---|---|---|---|---|---|
| 860,584 | A | | 5/1905 | Teufel | |
| 827,207 | A | * | 7/1906 | Boehm | 602/73 |
| 850,298 | A | * | 4/1907 | Mars | 602/71 |
| 1,119,944 | A | | 12/1914 | Fritsch | |
| 1,477,187 | A | * | 12/1923 | Rayne | 602/71 |
| 3,504,671 | A | | 4/1970 | Nelkin | |
| 4,526,167 | A | | 7/1985 | Ebenal | |
| 4,622,962 | A | * | 11/1986 | Kauffman | 602/70 |
| 5,036,839 | A | | 8/1991 | Weiss | |
| 5,094,234 | A | | 3/1992 | Searcy | |
| 5,237,706 | A | | 8/1993 | Nalbandian | |
| 5,243,974 | A | | 9/1993 | Allen | |
| 5,275,592 | A | | 1/1994 | Grizzaffi | |
| 6,061,840 | A | | 5/2000 | Alligator | |
| 2007/0180600 | A1 | | 8/2007 | Allemann | |

* cited by examiner

*Primary Examiner* — Michael A. Brown
(74) *Attorney, Agent, or Firm* — Galbreath Law Offices, P.C.; John A. Galbreath

(57) ABSTRACT

The invention is a support device for the male anatomy, comprising a pouch with an opening at the top for inserting the penis and testicles, a waistband to which the top front of the pouch is attached, and side straps. Each side strap is attached at one end to the waistband, and the side straps are attached at their other ends to substantially the same place on the top rear portion of the pouch.

20 Claims, 4 Drawing Sheets

ANATOMY SUPPORT DEVICE

CROSS-REFERENCES TO RELATED APPLICATIONS

Not Applicable.

BACKGROUND

1. Field of the Invention

The invention is in the area of devices that contain and support the male anatomy—for example jockstraps, athletic supporters, and the like.

2. Description of the Related Art

The prior art discloses various devices that contain and support the male anatomy. However, none of these patents exhibit the features of the present invention—that is, an anatomy support device having a pouch, waistband, and side straps, wherein the top of the pouch, at the front and sides, are attached to the waistband, and at the rear of the top of the pouch, there is an opening hanging down from the waistband, and two side straps are attached to substantially the same place on this opening.

U.S. Pat. No. 5,036,839 to Weiss discloses a pouch supporter—but the physical structure of this supporter differs significantly from the invention, in that Weiss's pouch only encloses the scrotum and not the penis. In addition, Weiss lacks any other supporting structure, such as a waistband or side straps—and in fact, Weiss's purpose is to avoid supporting structure other than his single strap that cinches the top of the pouch closed.

U.S. Pat. No. 1,119,944 to Fritsch; U.S. Pat. No. 3,504,671 to Nelkin; U.S. Pat. No. 5,243,974 to Allen; U.S. Pat. No. 860,584 to Teufel; U.S. Pat. No. 5,237,706 to Nalbandian; and U.S. Pat. No. 4,526,167 to Ebenal disclose supporters with side straps. However, in all these supporters, the side straps are attached at the bottom of the front panel—i.e., the side straps are attached in a way that is significantly different from the invention.

U.S. Pat. No. 5,094,234 to Searcy; U.S. Pat. No. 1,477,187 to Rayne; and U.S. Pat. No. 5,275,592 to Grizzaffi show supporters with straps that connect the top of the front panel or pouch to the waistband. However, in all these devices, the straps are attached in a manner that is significantly different from that of the invention.

U.S. Published Application 2007/0180600 (Allemann) shows a pouch for containing the male anatomy. However, Allemann does not disclose a waistband, side straps, or any other support structure. In fact, Allemann's fundamental purpose and objective is to avoid having a waistband, straps, or other support structure, and Allemann states this quite clearly in his disclosure. Similarly, U.S. Pat. No. 6,061,840 to Alligator shows a pouch for containing the male anatomy, but does not disclose side straps attached to substantially the same place on the bottom of an opening in the pouch, as in the invention.

SUMMARY OF THE INVENTION

The invention is a support device for the male anatomy, comprising a pouch with an opening at the top for inserting the penis and testicles, a waistband to which the top front of the pouch is attached, and side straps. Each side strap is attached at one end to the waistband, and the side straps are attached at their other ends to substantially the same place on the top rear portion of the pouch.

The side strap attachment configuration of the invention provides the best combination of support and comfort. This is a counterintuitive and surprising result, because ordinarily one would expect that the best stability and support would come from attaching the side straps to the pouch in a manner such that the side straps are spaced apart from each other—i.e., such that the side straps grip the top portion of the pouch at more than one place.

In addition, because the top rear portion of the pouch of the invention can hang down somewhat, as opposed to the top front portion of the pouch which is affixed to the waistband, this better accommodates the wearer's anatomy.

Further objects and advantages of the invention will become apparent from a consideration of the ensuing description and drawings.

DETAILED DESCRIPTION OF THE INVENTION

Figure 1:
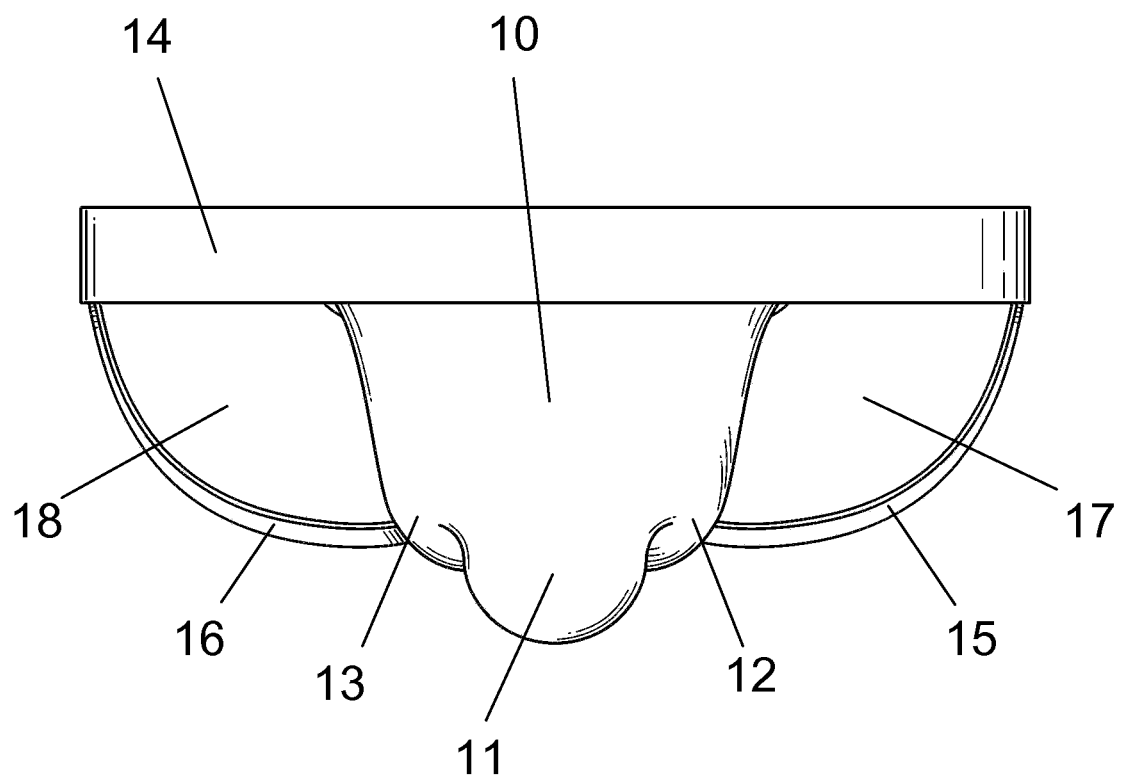
FIG. 1 is a front view of the anatomy support device of the invention, showing the pouch, waistband, and side straps.

The following provides a list of the reference characters used in the drawings:
10. Pouch
11. Penile containment chamber
12. Left testicle containment chamber
13. Right testicle containment chamber
14. Waistband
15. Left side strap
16. Right side strap
17. Left leg opening
18. Right leg opening
19. Waist opening
20. Hem
21. Pouch opening
22. Side strap anchor point
23. Stitches FIG. 1 illustrates the anatomy support device from the front perspective. It should be understood that when the ensuing description uses the terms "left" and "right", that refers to the wearer's left and right. Said another way, in FIG. 1, items on the left side of the view are on the right side from the wearer's perspective, and items on the right side of the view are on the left side from the wearer's perspective.

The device comprises a pouch 10 having a penile containment chamber 11, a left testicle containment chamber 12, and a right testicle containment chamber 13. These chambers are adapted to contain the penis and testicles of the wearer. A substantial portion of pouch 10 is attached at the top front thereof to a waistband 14, which in use encircles the midsection of the wearer's body. A left side strap 15 is attached at one end to the waistband and at the other end to the back of the pouch, as will be further described below. A right side strap 16 is attached at one end to the waistband and at the other end to the back of the pouch. Pouch 10, waistband 14, and left side strap 15 together bound a left leg opening 17, into which the wearer inserts his left leg when donning the device. Pouch 10, waistband 14, and right side strap 16 together bound a right leg opening 18, into which the wearer inserts his right leg when donning the device.

Figure 2:
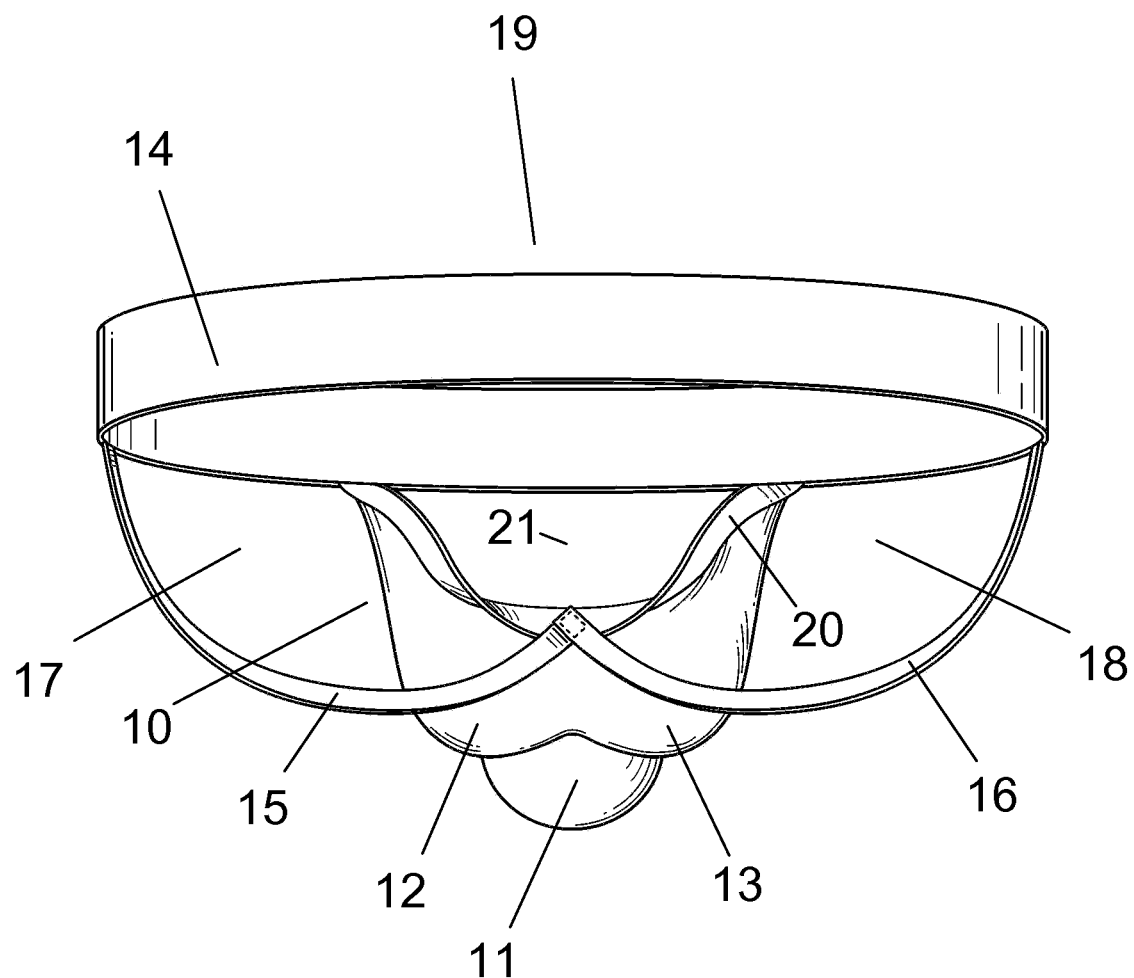
FIG. 2 is a back view of the anatomy support device of the invention.

FIG. 2 illustrates the anatomy support device from the back or rear perspective. The components of the device are as described above for FIG. 1. In addition, it can be seen that waistband 14 forms a waist opening 19, which in use contains the wearer's midsection. The top rear portion of pouch 10, that is, the top portion of pouch 10 which is not attached to waistband 14, has a hem 20 located thereon. It can be seen that the top rear portion of pouch 10 is open at pouch opening 21, thus providing access to the interior of the pouch. Left side strap 15 and right side strap 16 are attached to hem 20 at the rear of pouch opening 21, as will be more fully explained below.

Figure 3:
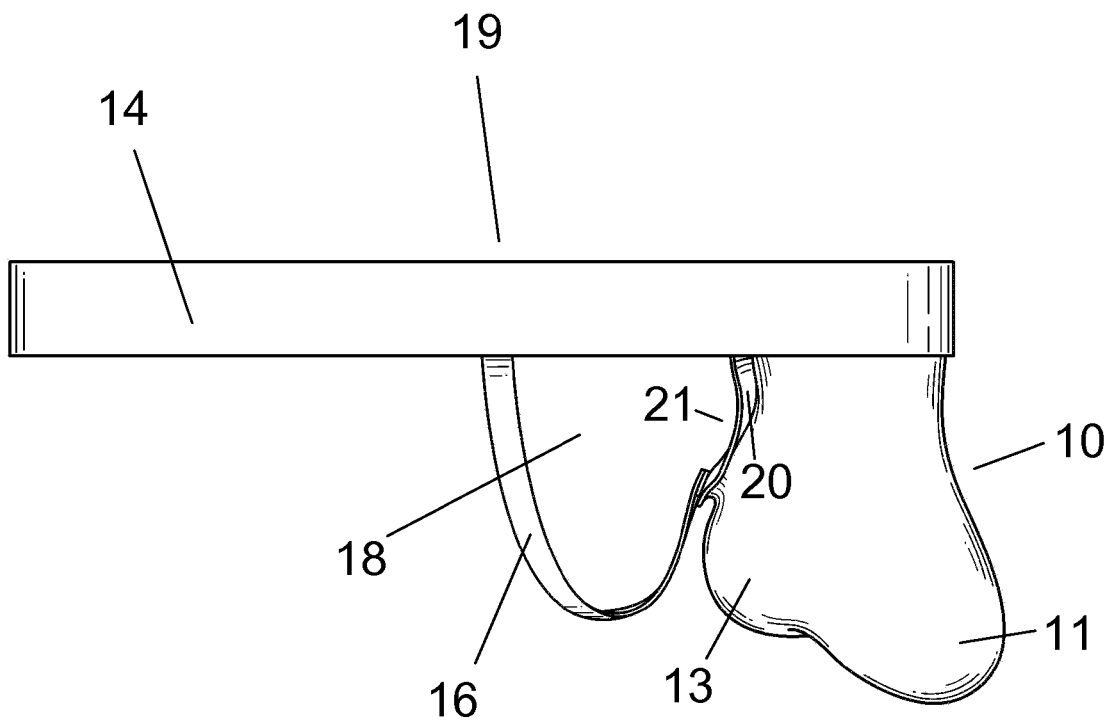
FIG. 3 is a right side view of the anatomy support device of the invention. The left side of the device is substantially the same as the right side.

FIG. 3 is a right side view of the anatomy support device. It can be seen that the top rear portion of pouch 10, being unattached to waistband 14, hangs down somewhat in order to better accommodate the wearer's anatomy—the testicles being below the base of the penis in the male anatomy. Right side strap 16 is attached at substantially the midpoint, front to rear, of waistband 14.

It can be appreciated from the other views that the left side of the device is substantially the same as the right side—that is, the left side view would be the same as the right side view, only "flipped" so that the pouch would be at the left side of the drawing page.

Figure 4:
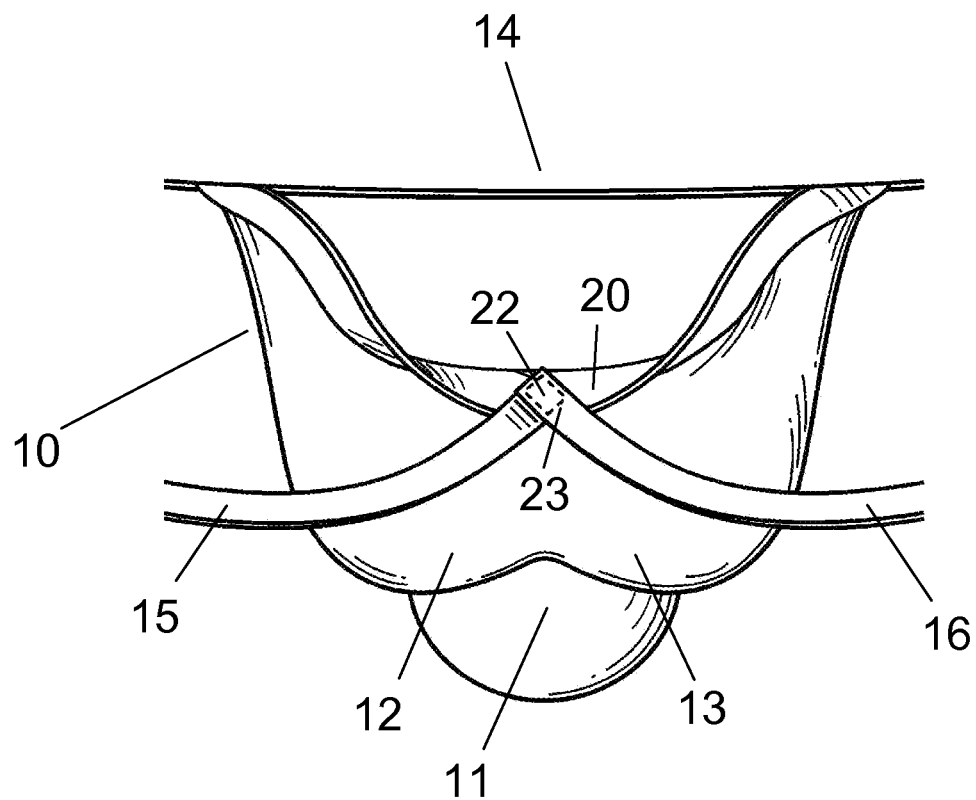
FIG. 4 is a detail back view of the anatomy support device of the invention, focused on the anchoring of the side straps on the top rear hem of the pouch.

FIG. 4 is another back view of the anatomy support device, showing in greater detail the anchoring of the side straps on the top rear hem of the pouch. Specifically, left side strap 15 and right side strap 16 are attached at substantially the same location on the top rear hem of the pouch, at side strap anchor point 22. Side strap anchor point 22 is located at substantially the midpoint, from side to side, of hem 20. Moreover, left side strap 15 and right side strap 16 are attached at side strap anchor point 22 in a cross-biased alignment. In other words, left side strap 15 and right side strap 16 are attached so that together they form substantially a right angle on the top rear hem of pouch 10. Further, left side strap 15 and right side strap 16 are attached to the inner part of hem 20—that is, they are attached on the side of hem 20 that is proximate to the interior of pouch 10 when the device is in use on the wearer's body. These aspects promote optimal anchoring of the side straps, and optimal support and comfort for the wearer.

In the FIG. 4 view, the side straps are attached using stitches 23; however, it should be understood that the attachment can be effected using other suitable means, including but not limited to adhesive, plastic or metal fasteners, and the like. Similarly, the front top of pouch 10, and the ends of side straps 15 and 16 that are not proximate to pouch 10, are attached to waistband 14 using stitches but may also be attached using other suitable means.

Pouch 10 is preferably constructed of knitted fabric, with no exposed seams on the interior of the pouch for maximum comfort. Waistband 14 and side straps 15 and 16 are preferably constructed of a suitably elastic material.

To use the device, the wearer inserts his left and right legs through left leg opening 17 and right leg opening 18 respectively, and pulls the device up his legs. When the device is proximate to the wearer's crotch, the wearer inserts his penis and testicles into penile containment chamber 11, left testicle containment chamber 12, and right testicle containment chamber 13 respectively, and adjusts waistband 14 comfortably about his midsection. The wearer's anatomy is thus firmly and comfortably supported during sporting or other activities.

While the above descriptions contain many specificities, these shall not be construed as limitations on the scope of the invention, but rather as exemplifications of embodiments thereof. Many other variations are possible without departing from the spirit of the invention.

Accordingly, the scope of the invention should be determined not by the embodiments illustrated, but by the appended claims and their legal equivalents.

What is claimed is:

1. An anatomy support device, comprising:
   (a) a pouch adapted to contain said anatomy, said pouch having a top front portion and a top rear portion;
   (b) the top front portion and top rear portion of said pouch defining an opening adapted for inserting said anatomy therethrough;
   (c) a penile containment chamber located on or within said pouch;
   (d) at least one testicle containment chamber located on or within said pouch;
   (e) a waistband, wherein the top front portion of said pouch is attached to said waistband;
   (f) a plurality of side straps each having a first end and a second end, said side straps being attached at their first ends to the waistband and at their second ends to substantially the same point on the top rear portion of said pouch.

2. The anatomy support device of claim 1, wherein two testicle containment chambers are located on or within said pouch.

3. The anatomy support device of claim 1, wherein said pouch has two sides, and both said side straps are attached at their second ends to the top rear portion of the pouch at substantially the midpoint, from side to side, of the pouch.

4. The anatomy support device of claim 3, wherein both said side straps are attached at their second ends to the interior top rear portion of the pouch.

5. The anatomy support device of claim 3, wherein a hem is located along the top rear portion of the pouch, extending from one side to the other of the pouch.

6. The anatomy support device of claim 5, wherein both said side straps are attached at their second ends to the hem at substantially the midpoint, from side to side, of the pouch.

7. The anatomy support device of claim 1, wherein the device has two said side straps.

8. The anatomy support device of claim 1, wherein the waistband has a front portion and a rear portion, and each said side strap is attached at substantially the midpoint, from front to rear, of the waistband.

9. The anatomy support device of claim 1, wherein the side straps are attached to the top rear portion of said pouch using stitches.

10. The anatomy support device of claim 1, wherein said pouch is constructed of knitted fabric, with no exposed seams on the interior thereof.

11. A supporter, comprising:
    (a) a pouch adapted to contain a wearer's penis and testicles, said pouch having a top front portion and a top rear portion;
    (b) the top front portion and top rear portion of said pouch defining an opening adapted for inserting said penis and testicles therethrough;
    (c) a waistband adapted to fit around the wearer's midsection, wherein the top front portion of said pouch is attached to said waistband;
    (d) a plurality of side straps each having a first end and a second end, said side straps being attached at their first ends to the waistband and at their second ends to substantially the same point on the top rear portion of said pouch.

12. The supporter of claim 11, wherein a penile containment chamber and two testicle containment chambers are located on or within said pouch.

13. The supporter of claim 11, wherein said pouch has two sides, and both said side straps are attached at their second ends to the top rear portion of the pouch at substantially the midpoint, from side to side, of the pouch.

14. The supporter of claim 13, wherein both said side straps are attached at their second ends to the interior top rear portion of the pouch.

15. The supporter of claim 13, wherein a hem is located along the top rear portion of the pouch, extending from one side to the other of the pouch.

16. The supporter of claim 15, wherein both said side straps are attached at their second ends to the hem at substantially the midpoint, from side to side, of the pouch.

17. The supporter of claim 11, wherein the device has two said side straps.

18. The supporter of claim 11, wherein the waistband has a front portion and a rear portion, and each said side strap is attached at substantially the midpoint, from front to rear, of the waistband.

19. The supporter of claim 11, wherein the side straps are attached to the top rear portion of said pouch using stitches.

20. The supporter of claim 11, wherein said pouch is constructed of knitted fabric, with no exposed seams on the interior thereof.

\* \* \* \* \*